(12) United States Patent
Mrohs

(10) Patent No.: US 10,543,177 B2
(45) Date of Patent: Jan. 28, 2020

(54) COMPOSITION AND METHOD FOR TREATING SKIN CONDITIONS

(71) Applicant: Kevin Mrohs, Alexandria, VA (US)

(72) Inventor: Kevin Mrohs, Alexandria, VA (US)

(*) Notice: Subject to any disclaimer, the term of this patent is extended or adjusted under 35 U.S.C. 154(b) by 5 days.

(21) Appl. No.: 15/827,323

(22) Filed: Nov. 30, 2017

(65) Prior Publication Data
US 2018/0289633 A1 Oct. 11, 2018

Related U.S. Application Data

(60) Provisional application No. 62/484,096, filed on Apr. 11, 2017.

(51) Int. Cl.
*A61K 31/045* (2006.01)
*A61K 31/573* (2006.01)
*A61P 31/22* (2006.01)
*A61K 47/44* (2017.01)
*A61K 9/00* (2006.01)

(52) U.S. Cl.
CPC .......... *A61K 31/045* (2013.01); *A61K 9/0014* (2013.01); *A61K 31/573* (2013.01); *A61K 47/44* (2013.01); *A61P 31/22* (2018.01); *A61K 2300/00* (2013.01)

(58) Field of Classification Search
CPC .... A61K 31/045; A61K 9/006; A61K 31/573; A61K 47/10; A61K 47/44; A61K 2300/00; A61P 31/22; A61P 9/0014
USPC ........................................................ 514/171
See application file for complete search history.

(56) References Cited

U.S. PATENT DOCUMENTS

2016/0030450 A1\* 2/2016 Kandavalli .......... A61K 9/0014
424/489

\* cited by examiner

*Primary Examiner* — Kristin A Vajda
(74) *Attorney, Agent, or Firm* — Foley & Lardner LLP

(57) ABSTRACT

Provided herein are compositions and related methods for the treatment of herpes simplex virus (HSV) induced blisters and resulting ulcerative lesions. The composition includes at least one antiviral agent that is a long-chain aliphatic compound, and at least one topical corticosteroid.

5 Claims, No Drawings

COMPOSITION AND METHOD FOR TREATING SKIN CONDITIONS

BACKGROUND OF THE INVENTION

I. Background About Disease State and Epidemiology

Herpes simplex virus (HSV) is a double-strand, lipid enveloped DNA virus which is a member of the Alphaherpesvirinae subfamily of the Herpesvirinae family of viruses. Other alphaherpesviruses include pseudorabies virus and varicella-zoster virus. HSV is classified into two subtypes, HSV-1 and HSV-2. HSV-1 is primarily responsible for orolabial infections, while HSV-2 is more prevalent in anogenital infections. In recent years, adolescents and younger patients are experiencing HSV-1 infection in the anogenital area as a result of changing sexual behaviors.

During initial infection, the virus is spread by direct skin to skin contact with an open lesion, or an infected individual. Infection can still occur after contact with asymptomatic infected individuals. Epithelial cells are initially infected. Systemic symptoms of primary infection can include fever, malaise, lymphadenopathy, and multiple ulcers. Upon initial infection, the virus will travel down a terminal sensory neuron, via complex interactions with viral surface proteins and transport motor proteins within the host, and remain latent in the nerve body. A complex array of immune components, including noncytolytic CD8+ cells secreting interferon-gamma, are responsible for maintaining latency. Once infected and latent, the virus remains in the host for life, as there are no curative measures to eliminate the virus at this point.

HSV is highly contagious and has infected significant numbers of people in the United States and throughout the world. According to the World Health Organization, an estimated 3.7 billion people under the age of 50 are infected with HSV-1. This is close to 67% of the global population, while estimates put infection in the Americas at about 40-50%. Furthermore, the incidence increases with age, with an estimated 90% of people over the age of 50 displaying HSV seropositivity. While many infections are asymptomatic for long periods of time, persistent HSV infection can lead to severely painful, debilitating, and disfiguring episodes.

Herpes labialis (also known as herpes simplex labialis or HSL) is primarily caused by HSV-1. The symptoms include a rash of the skin, usually involving the lips but can affect oral membranes, and are characterized by blisters with pain and occasional itching. There are different sequential stages of lesion that include prodromal period (erythema), followed by a papular stage, vesicle formation, ulceration, hard crust formation, loss of crust and dry flaking, and finally complete epithelization. Untreated, this cycle generally lasts 8-9 days. The prodromal period, with symptoms such as tingling, itching, or burning, precedes viral reactivation approximately 60% of the time, and can be an indication of a more severe episode.

Approximately, 20-40% of HSV seropositive patients experience recurrent herpes labialis (RHL), and recurrences can range from an aborted lesion (lesion does not progress beyond prodromal stage), to the classical ulceration and hard crust, to extensive lesions in immunocompromised patients. For those who experience RHL, 4 lesions per year is often typical, however some patients can experience ten or more. Ulcerative lesions often take longer to heal, and can adversely impact quality of life due to psychological and social issues. Patients with severe recurrences may skip work or social events due to the disfigurement and pain of the condition. There is also an increased severity and persistence of RHL in patients with AIDS. It is estimated that there are over 100 million episodes of RHL per year in the United States.

Currently, it is recommended that herpes labialis be treated with antivirals, including viral DNA polymerase inhibitors acyclovir, famciclovir, and valacyclovir. The aim of such antiviral therapy is to block viral replication to enable shortening the duration of symptoms and to accelerate healing of the lesion associated with herpes labialis. There are two types of antiviral therapy for the treatment of herpes labialis, topical and oral, which are available over the counter or as prescription-only (Cunningham, et al. J clin Virol. 2012 January; 53 (1); 6-11).

II. Background About Aliphatic Alcohols

Antiviral activities of aliphatic alcohols having from 20 to 32 carbons are disclosed in U.S. Pat. Nos. 4,874,794, 5,071,879, 5,166,219, 5,194,451 and 5,534,554.

Some compounds that are structurally related to long-chain aliphatic alcohols also have been associated with antiviral activity. For example, U.S. Pat. No. 4,513,008 discloses the virucidal activity of C20 to C24 linear polyunsaturated acids, aldehydes or alcohols having five to seven double bonds. Compounds having a long chain fatty acyl group, containing at least three or four unsaturated bonds, attached to a nucleoside or nucleoside analogue are disclosed as antiviral treatments in U.S. Pat. No. 5,216,142. Related U.S. Pat. No. 5,276,020 discloses antiviral compounds having a C16, C18 or C20 long chain fatty acid group attached to a nucleoside analogue and a method of treating virus infection using these compounds. U.S. patent application publication No. 2003/0073651 discloses the anti-viral activities of long-chain aliphatic compounds including C18 to C28 primary alcohols.

A C22 aliphatic alcohol, docosanol exhibits potent antiviral activity against viruses including herpes simplex virus, HIV-1 and respiratory syncytial virus in vitro and Friend virus in vivo (Katz, D. H., et al., Proc. Nat. Acad. Sci. USA 88:10825-10829, 1991; U.S. Pat. No. 5,534,554). The Abreva® cream (docosanol 10%) is a nonprescription over-the-counter (OTC) medicine approved by the FDA for treating herpes labialis.

Topical anti-inflammatory medicine may limit the local inflammation cascade in the skin, thus worsen skin infections by reducing the natural defense system against the infection (Prescrire Int. 2011 September; 20(119):205-7.). Corticosteroids are known to worsen certain viral infections and to cause superinfections in some cases. To date, there have been no clinical trials evaluating the effect of the combination of docosanol and an anti-inflammatory agent on the treatment of herpes labialis, nor is there any available product containing such a combination.

Currently treatments of herpes labialis have limited efficacy in preventing the recurrence of ulcerative lesions and reducing the duration of the illness. There exists a substantial need for new pharmaceutical products for treating herpes labialis. The present invention meets this need.

SUMMARY OF THE INVENTION

This invention relates to treatment of viral infections using long-chain aliphatic compounds in combination with corticosteroids, and more particularly to the topical application of therapeutic compositions containing docosanol in combination with hydrocortisone.

The present invention is based on the surprising and unexpected findings that a corticosteroid synergistically intensifies the antiviral activity of a long-chain aliphatic compound against HSV-induced conditions in the skin or mucosal membrane. The antiviral activity of a long-chain aliphatic compound when administered in combination with at least one corticosteroid is not merely additive; rather, the two compounds work synergistically to produce improved results.

In one aspect, provided herein are compositions for treating or preventing a viral-induced disorder in a skin or mucosal membrane of a subject. In some embodiments, the composition comprises: (a) a therapeutically effective amount of at least one long-chain aliphatic compound; and (b) a therapeutically effective amount of a corticosteroid.

In some embodiments, the long-chain aliphatic compound is selected from the group consisting of C18-C28 primary alcohols, stearyl alcohol, erucyl alcohol, brassidyl alcohol, arachidyl alcohol, docosane, docosanoic acid, erucamide, and mixtures thereof.

In some embodiments, the corticosteroid comprises hydrocortisone.

In some embodiments, the viral-induced disorder is herpes labialis or recurrent herpes labialis.

In some embodiments, the composition further comprises coconut oil.

In some embodiments, the composition comprises docosanol and hydrocortisone as the sole active ingredients, and optionally coconut oil as a pharmaceutically acceptable carrier.

In another aspect, provided herein are methods for treating a subject with a viral-induced disorder in a skin or mucosal membrane of a subject. In some embodiments, the method comprises a combination treatment of: (a) administering to the subject a therapeutic effective amount of at least one long-chain aliphatic compound; and (b) administering to the subject a therapeutically effective amount of a corticosteroid.

In some embodiments, the viral-induced disorder is caused by herpes simplex virus (HSV)-1, HSV-2, HSV-6, cytomegaloviru (CMV), Epstein-Barr virus (EBV), varicella zoster virus (VZV), influenza virus, human lymphotropic virus (HTLV), human immunodeficiency virus (HIV), papilloma virus and respiratory syncytial virus.

In some embodiments, the viral-induced disorder is caused by reactivation of latent HSV.

In some embodiments, the viral-induced disorder is herpes labialis or recurrent herpes labialis.

In some embodiments, the long-chain aliphatic compound is selected from the group consisting of C18-C28 primary alcohols, stearyl alcohol, erucyl alcohol, brassidyl alcohol, arachidyl alcohol, docosane, docosanoic acid, erucamide, and mixtures thereof.

In some embodiments, the at least one corticosteroid comprises hydrocortisone.

In some embodiments, the at least one long-chain aliphatic compound and the at least one corticosteroid are administered simultaneously or sequentially.

In some embodiments, the at least one long-chain aliphatic compound and the at least one corticosteroid are present in the same composition.

In some embodiments, administration of the at least one long-chain aliphatic compound and the the at least one corticosteroid are through topical application.

In some embodiments, upon administration, the at least one corticosteroid serves to: (1) reduce a viral titer in affected areas of a skin or mucosal membrane of the subject, or overall in the subject; (2) reduce a chance of developing ulcerative lesions in affected areas of a skin or mucosal membrane of the subject; (3) reduce epithelial damage in affected areas of a skin or mucosal membrane of the subject; (4) reduce the rate of recurrence of the viral-induced disorder in the subject; (5) reduce the duration of a recurrent episode of the viral-induced disorder in the subject; (6) reduce the healing time of ulcerative lesions in affected areas of a skin or mucosal membrane of the subject; (7) reduce pain in affected areas of a skin or mucosal membrane of the subject; (8) reduce the amount of the long-chain aliphatic compound needed for treating the viral-induced disorder; (9) reduce an adverse effect or reaction to the long-chain aliphatic compound in the subject; or any combination thereof.

In another aspect, provided herein are methods of preventing a viral-induced disorder in a skin or mucosal membrane of a subject who is at risk of the viral-induced disorder. In some embodiments, the method comprises a combination treatment of: (a) administering to the subject a therapeutic effective amount of at least one long-chain aliphatic compound; and (b) administering to the subject a therapeutically effective amount of a corticosteroid.

In some embodiments, the subject has been exposed to a condition associated with viral reactivation, or the subject is expected to be exposed to a condition associated with viral reactivation.

In some embodiments, the subject has exhibited at least one early symptom of the viral-induced disorder in the skin or mucosal membrane.

In some embodiments, the method comprises topically administering a composition comprising docosanol and hydrocortisone to a patient suffering from herpes labialis or recurrent herpes labialis.

DETAILED DESCRIPTION OF THE INVENTION

Certain long-chain aliphatic compounds, such as aliphatic alcohols, aliphatic alcohols, aliphatic alkanes and aliphatic acids, are known to have an anti-viral property. For example, the Abreva® cream (docosanol 10%) is a nonprescription over-the-counter (OTC) medicine approved by the FDA for treating herpes labialis caused by herpes simplex virus (HSV).

Anti-viral long-chain aliphatic compounds are considered to have a special mechanism of action, and are not expected to lead to viral resistance to the treatment. For example, docosanol has been shown to be effective in acyclovir-resistant HSV strains. Although the mechanism is not fully understood, docosanol likely interferes with viral infusion, transmembrane migration, entry into the cytoplasm, as well as migration to the nucleus of local epithelial cells. This viral blocking indirectly inhibits replication of the virus, and prevents damage to epithelium that is caused by cell lysis following viral replication. Particularly, progressive binding and uptake of docosanol by cells may account for its antiviral activity because pre-incubation of cells with the alcohol produces optimal antiviral activity. During incubation, 70% of the cell-associated docosanol is found in cell membranous components and the remainder is associated with soluble cell fractions (Katz, D. H., et al., Proc. Natl. Acad. Sci USA 88:10825-10829, 1991). Cell membrane incorporation of docosanol does not inhibit virus binding to the cell surface. Instead, early viral protein synthesis is inhibited more than 80% and viruses do not localize to nuclei (Marcelletti, J. F. et al., Drugs of the Future 17(19): 879-882, 1992). Although intracellular metabolic conversions of docosanol may account for its antiviral activity, the alcohol is not cytotoxic in concentrations up to 300 mM (Katz, D. H. et al., Annals N.Y. Acad. Sciences, 724:472-488, 1994). The mechanism of action of docosanol is different from nucleoside analog antivirals, such as acyclovir, famciclovir, and valacyclovir.

The present invention is based on the surprising discovery that combining a long-chain aliphatic compound with at least one corticosteroid synergistically increased the effectiveness in treating viral infection. The antiviral activity of a long-chain aliphatic compound when administered in combination with at least one corticosteroid is not merely additive; rather, the two compounds work synergistically to produce dramatic results.

Provided herein are pharmaceutical compositions for treating or preventing a viral-induced condition in the skin or mucosal membrane of a subject. The composition comprises, as the active ingredients, at least one long-chain aliphatic compound in combination with at least one corticosteroid in a pharmaceutically acceptable carrier. Also provided herein are methods for treating viral infections, comprising the administration of at least one long-chain aliphatic compound in conjunction with at least one corticosteroid.

Composition

The long-chain aliphatic compounds suitable for use in the present invention are selected from saturated aliphatic alcohols, mono-unsaturated aliphatic alcohols, aliphatic alkanes, mono-unsaturated aliphatic amides and aliphatic acids having a carbon chain length of 18 to 28 carbons (C18 to C28). In some embodiments, the composition comprises stearyl alcohol, erucyl alcohol, brassidyl alcohol, arachidyl alcohol, docosanol, docosane, docosanoic acid, erucamide and stearic acid, or mixtures thereof. In some embodiments, the long-chain aliphatic compound is docosanol. According to the present disclosure, the long-chain aliphatic compound may be used at concentrations in the range of about 0.05% to about 40%. In some embodiments, docosanol is used at a concentration in the range of about 1% to about 20%. In some embodiments, docosanol is used at a concentration of about 10%.

In some embodiments, the long-chain aliphatic compound may be used at concentrations in the range of about 0.05% to about 0.1%, about 0.1% to about 0.2%, about 0.2% to about 0.3%, about 0.3% to about 0.4%, about 0.4% to about 0.5%, about 0.5% to about 0.6%, about 0.6% to about 0.7%, about 0.7% to about 0.8%, about 0.9% to about 1%, about 1% to about 2%, about 2% to about 3%, about 3% to about 4%, about 4% to about 5%, about 5% to about 6%, about 6% to about 7%, about 7% to about 8%, about 8% to about 9%, about 9% to about 10%, about 10% to about 15%, about 15% to about 20%, about 25% to about 30%, or about 35% to about 40%.

Methods of synthesis of docosanol and erucyl alcohol (cis-13-docosen-1-ol) are known to those skilled in the art (e.g., see U.S. Pat. No. 4,186,211). Stearyl alcohol can be synthesized according to the method of Brown et al. (J. Am. Chem. Soc. 78:2582, 1956). Methods of synthesis of alkanes, aliphatic alcohols, amides and aliphatic acids are well known in the art (e.g., see A. Streitwieser, Jr. & C. H. Heathcock, Introduction to Organic Chemistry, 2nd ed., Macmillan Publishing Co., New York, N.Y., 1981, at pages 160, 243-247, 303-307, 311-312, 315-317, 401406, 447-453, 515-516, 544, 548-555, 604-605, 670, 753-754 and 950).

The corticosteroid in the present composition may be a member of a class of steroid hormones naturally produced in the adrenal cortex or produced synthetically. Corticosteroids are involved in a wide range of physiologic systems such as stress response, immune response and regulation of inflammation, carbohydrate metabolism, protein catabolism, blood electrolyte levels, and behavior. Corticosteroids are generally grouped into four classes, based on chemical structure. Group A corticosteroids (short to medium acting glucocorticoids) include hydrocortisone, hydrocortisone acetate, cortisone acetate, tixocortol pivalate, prednisolone, methylprednisolone, and prednisone. Group B corticosteroids include triamcinolone acetonide, triamcinolone alcohol, mometasone, amcinonide, budesonide, desonide, fluocinonide, fluocinolone acetonide, and halcinonide. Group C corticosteroids include betamethasone, betamethasone sodium phosphate, dexamethasone, dexamethasone sodium phosphate, and fluocortolone. Group D corticosteroids include hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate. Non-limiting examples of corticosteroids include, aldosternone, beclomethasone, beclomethasone dipropionate, betametahasone, betametahasone-21-phosphate disodium, betametahasone valerate, budesonide, clobetasol, clobetasol propionate, clobetasone butyrate, clocortolone pivalate, cortisol, cortisteron, cortisone, deflazacort, dexamethasone, dexamethasone acetate, dexamethasone sodium phosphate, diflorasone diacetate, dihydroxycortison, flucinonide, fludrocortisones acetate, flumethasone, flunisolide, flucionolone acetonide, fluticasone furate, fluticasone propionate, halcinonide, halpmetasone, hydrocortisone, hydroconrtisone acetate, hydrocortisone succinate, 16α-hydroxyprednisolone, isoflupredone acetate, medrysone, methylprednisolone, prednacinolone, predricarbate, prednisolone, prednisolone acetate, prednisolone sodium succinate, prednisone, triamcinolone, triamcinolone, and triamcinolone diacetate. As used herein, the term "corticosteroid" can include, but is not limited to, the following generic and brand name corticosteroids: cortisone (CORTONE™ ACETATE™, ADRESON™ ALTESONA™, CORTELAN™, CORTISTAB™, CORTISYL™, CORTOGEN™, CORTONE™, SCHEROSON™); dexamethasone-oral (DECADRON-ORAL™, DEXAMETH™, DEXONE™, HEXADROL-ORAL™, DEXAMETHASONE™ INTENSOL™, DEXONE 0.5™, DEXONE 0.75™, DEXONE 1.5™, DEXONE 4™); hydrocortisone-oral (CORTEF™, HYDROCORTONE™); hydrocortisone cypionate (CORTEF ORAL SUSPENSION™); methylprednisolone-oral (MEDROL-ORAL™); prednisolone-oral (PRELONE™, DELTA-CORTEF™, PEDIAPRED™, ADNISOLONE™, CORTALONE™, DELTACORTRIL™, DELTASOLONE™, DELTASTAB™, DI-ADRESON F™ ENCORTOLONE™, HYDROCORTANCYL™, MEDISOLONE™, METI-CORTELONE™, OPREDSONE™, PANAAF-CORTELONE™, PRECORTISYL™, PRENISOLONA™ SCHERISOLONA™, SCHERISOLONE™); prednisone (DELTASONE™, LIQUID PRED™ METICORTEN™, ORASONE 1™, ORASONE 5™, ORASONE 10™, ORASONE 20™, ORASONE 50™, PREDNICEN-M™, PREDNISONE INTENSOL™, STERAPRED™, STERAPRED DS™, ADASONE™, CARTANCYL™, COLISONE™, CORDROL™, CORTAN™, DACORTIN™, DECORTIN™, DECORTISYL™, DELCORTIN™, DELLACORT™, DELTADOME™, DELTACORTENE™, DELTISONA™, DIADRESON™ ECONOSONE™, ENCORTON™, FERNISONE™, NISONA™, NOVO-PREDNISONE™ PANAFCORT™, PANASOL™, PARACORT™, PARMENISON™, PEHACORT™, PREDELTIN™, PREDNICORT™, PREDNICOT™, PREDNIDIB™, PREDNIMENT™, RECTODELT™, ULTRACORTEN™, WINPRED™); triamcinoloneoral (KENACORT™, ARISTOCORT™, ATOLONE™, SHOLOG A™, TRAMACORT-DTH, TRI-MED™, TRI-AMCOT™, TRISTOPLEX™, TRYLONE D™, U-TRI-LONE™). In some embodiments, a corticosteroid can be a corticosteroid which is active when applied topically, including, but not limited to clobetasol propionate, betamethasone valerate, betamethasone dripropionate, and mometasone furoate. In some embodiments, a corticosteroid can be prednisone (e.g. a compound having the structure of Formula V); prednisolone (e.g. a compound having the structure of Formula VI); triamcinolone (e.g. a compound having the structure of Formula VII); clobetasol propionate (e.g. a compound having the structure of Formula VIII); betamethasone valerate (e.g. a compound having the structure of Formula IX); betamethasone dipropionate (e.g. a compound having the structure of Formula X); or mometasone furoate (e.g. a compound having the structure of Formula XI). Methods of synthesizing steroids and corticosteroids are well known in the art and such compounds are also commercially available, e.g. predinsone (Cat. No. P6254, Sigma-Aldrich; St. Louis, Mo.).

In some embodiments, the corticosteroid is present at a concentration in arrange of about 0.1% to about 10%. In some embodiments, hydrocortisone or an analog thereof is used at a concentration in the range of about 0.1% to about 10%. In some embodiments, hydrocortisone is used at a concentration of 1%.

In some embodiments, hydrocortisone or an analog thereof is used at a concentration in the range of about 0.1% to about 0.2%, about 0.2% to about 0.3%, about 0.3% to about 0.4%, about 0.4% to about 0.5%, about 0.5% to about 0.6%, about 0.6% to about 0.7%, about 0.7% to about 0.8%, about 0.9% to about 1%, about 1% to about 2%, about 2% to about 3%, about 3% to about 4%, about 4% to about 5%, about 5% to about 6%, about 6% to about 7%, about 7% to about 8%, about 8% to about 9%, or about 9% to about 10%.

In some embodiments, the present composition is for topical administration, including but are not limited to direct application of a therapeutically effective amount of the one or more active ingredient on top of a skin or membrane of a subject. In some embodiments, the active ingredients are combined with a carrier that is physiologically compatible with the skin and membrane tissue of a human or animal to which it is administered. For example, the carrier may be substantially inactive except for surfactant properties used in making a suspension of the active ingredients. The compositions may include other physiologically active constituents that do not interfere with the efficacy of the saturated aliphatic alcohols, mono-unsaturated aliphatic alcohols, aliphatic alkanes, aliphatic acids and corticosteroids. An exemplary composition is disclosed in U.S. Pat. No. 3,592,930. The composition may further include one or more penetration enhancer capable of maximizing topical penetration, permeation, and retention of an active ingredient (such as corticosteroid), but prevents or reduces the systemic absorption. An exemplary composition is disclosed in Kircik et al. J Clin Aesthet Dermatol. 2017; 10(2): 12-19.

Suitable carriers include aqueous and oleaginous carriers such as, for example, white petrolatum, isopropyl myristate, lanolin or lanolin alcohols, mineral oil, coconut oil, sorbitan mono-oleate, propylene glycol, cetylstearyl alcohol (together or in various combinations), with a detergent (e.g., polyoxyl stearate or sodium lauryl sulfate) and mixed with water to form a lotion, gel, cream or semi-solid composition. Other suitable carriers comprise mixtures of emulsifiers and emollients with solvents such as sucrose stearate, sucrose cocoate, sucrose distearate, mineral oil, coconut oil, propylene glycol, 2-ethyl-1,3-hexanediol, polyoxypropylene-15-stearyl ether and water. Preservatives may also be included in the carrier including methylparaben, propylparaben, benzyl alcohol and ethylene diamine tetraacetate salts. Dilute suspensions without thickeners are most suitable for delivery to skin surfaces as aerosol sprays, using well known methods of delivery. The composition may also include a plasticizer such as glycerol or polyethylene glycol (molecular weight 800 to 20,000) and penetration enhancers, such as elaidyl alcohol, hexanol, dodecanol, and oleyl alcohol. The composition of the carrier can be varied so long as it does not interfere with the pharmacological activity of the active ingredients.

In some embodiments, the composition comprises, (1) as the sole active ingredients, docosanol and hydrocortisone. In some embodiments, the composition is a topical formulation comprising, (1) as the sole active ingredients, docosanol and hydrocortisone, and (2) as a pharmaceutically acceptable carrier, coconut oil. In some embodiments, the composition is a topical formulation comprising, (1) as the sole active ingredients, docosanol and hydrocortisone, (2) as a pharmaceutically acceptable carrier, coconut oil and oleyl alcohol. In some embodiments, the composition comprises about 1% to about 20% by weight of docosanol, and about 0.1% to about 10% by weight hydrocortisone. In some embodiments, the composition comprises about 1% hydrocortisone and about 10% docosanol.

The compositions may also include anti-microbial agents, other antiviral agents, anti-fungal agents, antioxidants, buffering agents, sunscreens and cosmetic agents such as coloring agents, fragrances, lubricants and moisturizers or drying agents. Anti-microbial agents useful for inclusion in the compositions include polymyxin B and tetracycline. Other antiviral agents included in the formulations may be cytokines. Anti-fungal agents that may be included are micatin or tolnaftate. Antioxidants such as vitamin E may be included. Sunscreens such as para-aminobenzoic acid may be included. Anti-histamine agents useful for inclusion in the compositions include, for example, doxylamine, pramoxine, diphenhydramine. Drying agents that may be included. Lubricants such as synthetic or natural beeswax may also be included. Thickening agents added to the compositions may include pullulin, xanthan, polyvinylpyrrolidone or carboxymethylcellulose.

Therapeutic formulations of the present invention may be prepared for storage by mixing one or more therapeutic agents or components (e.g., at least one long-chain aliphatic compounds with at least one corticosteroid) having the desired degree of purity with optional physiologically acceptable carriers, excipients, or stabilizers (Remington's Pharmaceutical Sciences, 16th edition, Osol, A., Ed., (1980)), in the form of lyophilized cake or aqueous solutions. Acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues)

polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween®, Pluronics™ or polyethylene glycol (PEG).

Method of Treatment

The present disclosure encompasses methods of treating or preventing a viral infection comprising administering to a subject in need therapeutically effective amount of at least one long-chain aliphatic compound and a therapeutically effective amount of at least one corticosteroid for a period of treatment to achieve the desired therapeutic effect. The subject is preferably a mammal, including but not limited to, animals such as cows, pigs, horses, chickens, cats, dogs, etc. Most preferably the subject is human.

Administrations of long-chain aliphatic compounds have been shown to elicit activities against virus implicated in infections of skin. The anti-viral mechanism of action of the long-chain aliphatic compounds is considered to be different from nucleoside analog antivirals, such as acyclovir, famciclovir, and valacyclovir, and is not expected to lead to viral resistance to the treatment. For example, docosanol has been shown to be effective in acyclovir-resistant HSV strains. Although the mechanism is not fully understood, docosanol likely interferes with viral infusion, transmembrane migration, entry into the cytoplasm, as well as migration to the nucleus of local epithelial cells. This viral blocking indirectly inhibits replication of the virus, and prevents damage to epithelium that is caused by cell lysis following viral replication.

However, it is completely unexpected and surprising discovery that combining a long-chain aliphatic compound with one or more corticosteroid dramatically increased the effectiveness of the long-chain aliphatic compounds in treating viral infection. As shown in the examples below, the antiviral activity of a long-chain aliphatic compound when administered in combination with at least one corticosteroid is not merely additive; rather, the two compounds work synergistically to produce dramatic results.

The method of the present invention includes administration of a composition comprising active ingredients and pharmaceutically acceptable carrier to a subject to treat or prevent viral infection. In some embodiments, the method comprises administering to a subject in need thereof a therapeutically effective amount of at least one long-chain aliphatic compound and at least one corticosteroid.

In some embodiments, administration of the long-chain aliphatic compound and the corticosteroid is to the skin or a mucous membrane of the subject in need using a topical formulation comprising (1) the long-chain aliphatic compound as the sole active ingredient; (2) the corticosteroid as the sole active ingredient; or (3) the long-chain aliphatic compound and the corticosteroid as the sole active ingredients. The topical formulation can include, but are not limited to a cream, lotion, gel, ointment, suspension, aerosol spray or semi-solid formulation (e.g., a suppository).

In some embodiments, application of the topical formulation may be one to ten applications of 10 mg to 10 g per application for one to fourteen days. In some embodiments, application of the formulation may be once every twelve hours and up to once every four hours. In some embodiments, two to five applications of the composition per day, of about 0.1 g to 5 g per application, for one to seven days are sufficient to prevent or treat a viral infection. For topical applications, the compositions are preferably applied to lesions daily as soon as symptoms (e.g., pain, swelling, itching or inflammation) are detected. Where topical or transmembrane penetration is employed as a route of administration, the composition may optionally contain a penetration enhancer, including but are not limited to azone, dimethylsulfoxide, oleyl alcohol.

For the treatment of disease, the appropriate dosage of the aliphatic compound and of the corticosteroid will depend on the type of disease to be treated, the severity and course of the disease, previous therapy, the patient's clinical history and response to the treatment methods disclosed herein, and the discretion of the attending physician.

In some embodiments, the long-chain aliphatic compound is administered from about 1 ng/kg up to about 2000 ng/kg per one topical application, or less than about 2000 ng/kg per one topical application. In some embodiments, the corticosteroid is administered from about 1 ng/kg up to about 2000 ng/kg per one topical application, or less than about 2000 ng/kg per one topical application.

In various embodiments, administration of the at least one long-chain aliphatic compound and the at least one corticosteroid can be achieved by co-formulation into one formulation for simultaneous administration. In other embodiments, the at least one long-chain aliphatic compound and the at least one corticosteroid can be formulated separately for administration simultaneously or sequentially. The methods and routes for administration of long-chain aliphatic compound and the corticosteroid component of the present combination therapy can be the same or different.

In some embodiments, the long-chain aliphatic compound is administered as a mainstay treatment for infection and is administered multiple times during a period of treatment. The corticosteroid can be administered as a single dose or a plurality of separated doses throughout the period of treatment.

As used herein, "a period of treatment" or "treatment period" refers to the time period starting with the initiation of a treatment, such as the initial administration of a therapeutic agent or drug to a treated subject, and ending with the lapse of any observable therapeutic effect in the subject originated from the treatment, such as the end of metabolism and/or clearance of the administered therapeutics from the subject's system. The period of treatment can be for any therapeutically effective duration of time following the initiation of the treatment, such as but not limited to, 1 day up to 2 weeks or any time point in between, including for example 1 day, 2 days, 3 days, 4 days, 5 days, 6 days, 7 days, 8 days, 9 days, 10 days, 11 days, 12 days, 13 days, and 14 days. In some embodiments, the period of treatment can be longer, such as up to 1 month, up to 2 months, up to 3 months, or up to 6 months or up to 1 year. In some embodiments, the period of treatment is no longer than 2 weeks.

In some embodiments, the present treatment can begin as soon as an early sign of viral infection or reactivation is noticed. As used herein, viral reactivation refers to the process by which a virus in a latent phase switches to a lytic phase of replication, which may be provoked by a combination of external and/or internal cellular stimuli. Such early signs of viral infection or reactivation include but are not limited to itching, skin redness, swelling and other signs of inflammation.

In some embodiments, the present combination therapy can be used in methods of preventing viral infections. For example, certain patient populations are at risk for developing a viral infection such as patients or patients traveling to certain parts of the world known to harbor certain microbes, and patient who has been in contact with people known to be infected by the virus. Patients who have been confirmed to be seropositive for a virus, or who have had previous episodes of viral reactivation are at risk of developing diseased symptoms caused by the virus, especially when such patients have been or will be exposed to external and/or internal stimuli that trigger the viral reactivation. In some embodiments, ultraviolet radiation, stress, hormonal changes, febrile illness, and trauma may trigger reactivation of latent HSV, and cause HSV-induced skin or membrane conditions in the patient, such as developing herpes labialis.

In some embodiments, the at least one long-chain aliphatic compound and the at least one corticosteroid can be administered in a time frame selected from the group consisting of: (a) within about 36 hours of each other; (b) within about 12 hours of each other; or (c) within about 6 hours of each other.

In some embodiments, the present compositions and methods are useful for preventing or treating a variety of viral infections such as those caused by herpesviruses including (HSV) such as HSV-1, HSV-2 and HSV-6, cytomegalovirus (CMV), Epstein-Barr virus (EBV) and varicella zoster virus (VZV), influenza virus, human lymphotropic viruses (e.g., HTLV-1), human immunodeficiency viruses (e.g., HIV-1), papilloma virus and respiratory syncytial virus. In some embodiments, the present compositions and methods are useful for preventing or treating disorder in a subject's skin or mucosal membrane caused by reactivation of HSV. In some embodiments, the present compositions and methods are useful for preventing or treating herpes labialis or recurrent herpes labialis (RHL).

In some embodiments, the compositions are useful for preventing or treating an episode of reactivation of latent HSV infection, such as an episode of recurrent herpes labialis. In some embodiments, the present methods effectively (1) reduce the viral titer overall in a treated subject, particularly for systemic treatment, and/or in lesions of affected areas of the skin or mucous membrane, particularly for topical treatment; (2) reduce a chance of developing ulcerative lesions in affected areas of the skin or mucosal membrane; (3) reduce epithelial damage in affected areas of the skin or mucosal membrane; (4) reduce the rate of recurrence of the condition; (5) reduce the duration of a recurrent episode of the condition; (6) reduce the healing time of ulcerative lesions in affected areas of the skin or mucosal membrane; (7) reduce pain in affected areas of the skin or mucosal membrane; (8) reduce the amount of an active ingredient of a composition needed for treating the condition; and/or (8) reduce an adverse effect or reaction to an active ingredient of a composition.

The long-chain aliphatic compounds suitable for use in the present invention are selected from saturated aliphatic alcohols, mono-unsaturated aliphatic alcohols, aliphatic alkanes, mono-unsaturated aliphatic amides and aliphatic acids having a carbon chain length of 18 to 28 carbons (C18 to C28). In some embodiments, the composition comprises stearyl alcohol, erucyl alcohol, brassidyl alcohol, arachidyl alcohol, docosanol, docosane, docosanoic acid, erucamide and stearic acid, or mixtures thereof. In some embodiments, the long-chain aliphatic compound is docosanol.

The corticosteroid in the present composition may be a member of a class of steroid hormones naturally produced in the adrenal cortex or produced synthetically. Corticosteroids are involved in a wide range of physiologic systems such as stress response, immune response and regulation of inflammation, carbohydrate metabolism, protein catabolism, blood electrolyte levels, and behavior. Corticosteroids are generally grouped into four classes, based on chemical structure. Group A corticosteroids (short to medium acting glucocorticoids) include hydrocortisone, hydrocortisone acetate, cortisone acetate, tixocortol pivalate, prednisolone, methylprednisolone, and prednisone. Group B corticosteroids include triamcinolone acetonide, triamcinolone alcohol, mometasone, amcinonide, budesonide, desonide, fluocinonide, fluocinolone acetonide, and halcinonide. Group C corticosteroids include betamethasone, betamethasone sodium phosphate, dexamethasone, dexamethasone sodium phosphate, and fluocortolone. Group D corticosteroids include hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate. Non-limiting examples of corticosteroids include, aldosternone, beclomethasone, beclomethasone dipropionate, betametahasone, betametahasone-21-phosphate disodium, betametahasone valerate, budesonide, clobetasol, clobetasol propionate, clobetasone butyrate, clocortolone pivalate, cortisol, cortisteron, cortisone, deflazacort, dexamethasone, dexamethasone acetate, dexamethasone sodium phosphate, diflorasone diacetate, dihydroxycortison, flucinonide, fludrocortisones acetate, flumethasone, flunisolide, flucionolone acetonide, fluticasone furate, fluticasone propionate, halcinonide, halpmetasone, hydrocortisone, hydroconrtisone acetate, hydrocortisone succinate, 16α-hydroxyprednisolone, isoflupredone acetate, medrysone, methylprednisolone, prednacinolone, predricarbate, prednisolone, prednisolone acetate, prednisolone sodium succinate, prednisone, triamcinolone, triamcinolone, and triamcinolone diacetate. As used herein, the term "corticosteroid" can include, but is not limited to, the following generic and brand name corticosteroids: cortisone (CORTONE™ ACETATE™, ADRESON™ ALTESONA™, CORTELAN™, CORTISTAB™, CORTISYL™, CORTOGEN™, CORTONE™, SCHEROSON™); dexamethasone-oral (DECADRON-ORAL™, DEXAMETH™, DEXONE™, HEXADROL-ORAL™, DEXAMETHASONE™ INTENSOL™, DEXONE 0.5™, DEXONE 0.75™, DEXONE 1.5™, DEXONE 4™); hydrocortisone-oral (CORTEF™, HYDROCORTONE™); hydrocortisone cypionate (CORTEF ORAL SUSPENSION™); methylprednisolone-oral (MEDROL-ORAL™); prednisolone-oral (PRELONE™, DELTA-CORTEF™, PEDIAPRED™, ADNISOLONE™, CORTALONE™, DELTACORTRIL™, DELTASOLONE™, DELTASTAB™, DI-ADRESON F™ ENCORTOLONE™, HYDROCORTANCYL™, MEDISOLONE™, METICORTELONE™, OPREDSONE™, PANAAF-CORTELONE™, PRECORTISYL™, PRENISOLONA™ SCHERISOLONA™, SCHERISOLONE™); prednisone (DELTASONE™, LIQUID PRED™ METICORTEN™, ORASONE 1™, ORASONE 5™, ORASONE 10™, ORASONE 20™, ORASONE 50™, PREDNICEN-M™, PREDNISONE INTENSOL™, STERAPRED™, STERAPRED DS™, ADASONE™, CARTANCYL™, COLISONE™, CORDROL™, CORTAN™, DACORTIN™, DECORTIN™, DECORTISYL™, DELCORTIN™, DELLACORT™, DELTADOME™, DELTACORTENE™, DELTISONA™, DIADRESON™ ECONOSONE™, ENCORTON™, FERNISONE™, NISONA™, NOVO-PREDNISONE™ PANAFCORT™, PANASOL™, PARACORT™, PARMENISON™, PEHACORT™, PREDELTIN™, PREDNICORT™, PREDNICOT™, PREDNIDIB™, PREDNIMENT™, RECTODELT™, ULTRACORTEN™, WINPRED™); triamcinoloneoral (KENACORT™, ARISTOCORT™, ATOLONE™, SHOLOG A™, TRAMACORT-DTH, TRI-MED™, TRI-AMCOT™, TRISTOPLEX™, TRYLONE D™, U-TRI-LONE™). In some embodiments, a corticosteroid can be a corticosteroid which is active when applied topically, including, but not limited to clobetasol propionate, betamethasone valerate, betamethasone dripropionate, and mometasone furoate. In some embodiments, a corticosteroid can be prednisone (e.g. a compound having the structure of Formula V); prednisolone (e.g. a compound having the structure of Formula VI); triamcinolone (e.g. a compound having the structure of Formula VII); clobetasol propionate (e.g. a compound having the structure of Formula VIII); betamethasone valerate (e.g. a compound having the structure of Formula IX); betamethasone dipropionate (e.g. a compound having the structure of Formula X); or mometasone furoate (e.g. a compound having the structure of Formula XI).

Definitions

The terms "herpes labialis" and "herpes simplex labialis" are terms of art, which refer to a infective condition of the skin or mucosal membrane in a subject primarily caused by HSV-1. "Recurrent herpes labialis (RHL)" refers to recurrent episodes of herpes labialis, also known as cold sores.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

The terms "decrease", "reduced", "reduction", or "inhibit" are all used herein generally to mean a decrease by a statistically significant amount. However, for avoidance of doubt, "reduced", "reduction", "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference level), or any decrease between 10-100% as compared to a reference level. In the context of a marker or symptom, term refers to a statistically significant decrease in such level. The decrease can be, for example, at least 10%, at least 20%, at least 30%, at least 40% or more, and is preferably down to a level accepted as within the normal range for an individual without such disorder.

The terms "increased", "increase", "enhance", or "activate" are all used herein to generally mean an increase by a statically significant amount; for the avoidance of doubt, the terms "increased", "increase", "enhance", or "activate" mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the term "active ingredient" refers to the agent or component of a composition that is accountable for the desired therapeutic effect of the composition. In the context of the present disclosure, an active ingredient is included in a pharmaceutical composition or administered to a subject at a therapeutic effective dosage to elicit a biological effect of inhibiting a virus, or modulating an inflammatory response to the viral infection in the host.

As used herein, the term "pharmaceutical composition" refers to one or more active ingredient in combination with a pharmaceutically acceptable carrier, such as a carrier commonly used in the pharmaceutical industry.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the terms "pharmaceutically acceptable carrier" and "physiologically acceptable carrier" which may be interchangeably used refer to a carrier or a diluent that does not cause significant irritation to an organism and does not abrogate the biological activity and properties of the active ingredient. An adjuvant is included under these phrases.

As used herein, the term "administering," refers to the placement of a compound as disclosed herein into or onto a subject by a method or route which results in at least partial delivery of the agent at a desired site.

As used herein, the terms "therapeutically effective amount" "therapeutic amount" and "effective amount" are used interchangeably to refer to an amount of the administered therapeutic agent that will relieve or prevent to some extent one or more of the symptoms of the disorder being treated. An effective amount of a long-chain aliphatic compound or a corticosteroid for treating a viral infection is an amount that helps the treated subject to reach one or more desired clinical end points.

As used herein, the terms "treat," "treatment," "treating," or "amelioration" refer to therapeutic treatments, wherein the object is to reverse, alleviate, ameliorate, inhibit, slow down or stop the progression or severity of a condition associated with a viral infection. The term "treating" includes reducing or alleviating at least one adverse effect or symptom of a condition, disease or disorder associated with a virus-induced disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment). The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

EXAMPLES

Example 1. Storage and Handling

Docosanol: Docosanol is available as waxy, colorless, granules. Docosanol were stored and handled according to the material safety and data sheet provided by the manufacturer. Docosanol suspensions and creams were very stable. Stability testing yielded a beyond-use date (BUD) of at least 1 year.

Hydrocortisone: Hydrocortisone is available as a white, granular powder. Hydrocortisone was stored in a cool, dry place free from contaminants before it was used for compounding and according to the material data and safety sheet provided by the manufacturer.

Prepared combination product: A composition of docosanol and hydrocortisone was stored in a cool (20-25° C.), dry place free from contaminants. A BUD of 30 days was used for prepared compositions, as the cold cream used in the formulation was an aqueous, semi-solid formulation. Appropriate labeling that adheres to federal and local regulations was prepared.

Example 2. Product Preparation

Docosanol and hydrocortisone were obtained in a >95% purity powder from an FDA approved chemical distributor. Coconut oil was used as a levigating agent to enhance miscibility of the highly hydrophobic docosanol powder. To prepare a 0.1 oz cream (2.835 g) containing 10% docosanol and 1% hydrocortisone, the following formula was used on a patient-per-patient basis:
1. Measure 283.5 mg of docosanol granules on an electronic mass balance
2. Measure 2.835 mg of hydrocortisone powder on an electronic mass balance.
3. Weigh out 2548.6 mg of Cold Cream on an electronic mass balance
4. Levigate docosanol granules into a fine powder in a porcelain mortar and pestle with a small drop of coconut oil.
5. Add hydrocortisone powder into docosanol powder through geometric dilution and mix well until a uniform powder is created.
6. Place a cold cream on center of a compounding slab.
7. Levigate hydrocortisone and docosanol mixture into cold cream until a smooth, homogenous matrix is present.
8. Transfer cream preparation onto a weigh boat and measure 2.835 g.
9. Transfer entirety of 2.835 g cream preparation into plastic jar.

Document all investigational agent preparation on the appropriate compounding documentation provided.

Example 3. Measurement of Clinical Efficacy

The clinical evaluation end-point of herpes labialis includes the episode duration. Episode duration was measured from the time of the patient-initiated start of treatment of an episode until the time of loss of hard-crust for ulcerative lesions and to normal skin for non-ulcerative lesions. Additional end-points to evaluate include time to reduce a pain, the cumulative lesion size or epithelial damage, and the recurrence rate of ulcerative lesions.

The Mann-Whitney U statistical test was utilized to determine the difference in cold sore staging reported by patients receiving either docosanol alone or combination of docosanol and hydrocortisone.

Healing Time for Ulcerative Lesions

Patients are expected to show a significant reduction of several hours to 3 days in the healing time for ulcerative lesions in the combination therapy group compared to the placebo group or antiviral group alone. The outcome was observed on the basis of the healing time from the first sign of lesion until complete epithelization.

Pain Control and Tenderness in the Lesion

Patients are expected to show a significant reduction in pain and tenderness when the combined therapy was compared with antiviral alone.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A composition for treating or preventing a viral-induced disorder in a skin or mucosal membrane of a subject comprising:
    (a) a therapeutically effective amount of at least one long-chain aliphatic compound wherein the at least one long-chain aliphatic compound is selected from the group consisting of docosanol, erucyl alcohol, brassidyl alcohol, arachidyl alcohol, docosane, docosanoic acid, erucamide, and mixtures thereof; and
    (b) a therapeutically effective amount of a corticosteroid.

2. The composition of claim 1, wherein the corticosteroid comprises hydrocortisone.

3. The composition of claim 1, wherein the viral-induced disorder is herpes labialis or recurrent herpes labialis.

4. The composition of claim 1, wherein the composition further comprises coconut oil.

5. The composition of claim 1, comprising docosanol and hydrocortisone as the sole active ingredients, and optionally coconut oil as a pharmaceutically acceptable carrier.

* * * * *